United States Patent [19]
Atkins et al.

[11] Patent Number: 5,323,900
[45] Date of Patent: Jun. 28, 1994

[54] APPARATUS FOR STORING USED MEDICAL NEEDLES

[75] Inventors: Joseph R. Atkins, Dayton; Kathleen J. Scarbrough, Piqua, both of Ohio

[73] Assignee: Hawk Tool & Mold Inc., Englewood, Ohio

[21] Appl. No.: 977,080

[22] Filed: Nov. 16, 1992

[51] Int. Cl.$^5$ .................. B65D 85/24; B65D 25/24
[52] U.S. Cl. .................. 206/365; 206/366; 248/225.1; 248/224.1
[58] Field of Search .............. 248/223.4, 225.1, 224.1; 206/364, 365, 366, 367, 370; 604/192, 263

[56] References Cited

U.S. PATENT DOCUMENTS

| | | | |
|---|---|---|---|
| 3,329,146 | 7/1967 | Waldman, Jr. | 604/192 |
| 3,915,189 | 10/1975 | Holbrook et al. | 248/223.4 X |
| 4,613,135 | 9/1986 | Rush | 248/225.1 X |
| 4,623,336 | 11/1986 | Pedicano et al. | 604/192 |
| 4,917,243 | 4/1990 | Abrams et al. | 206/365 |
| 4,989,307 | 2/1991 | Sharpe et al. | 206/366 X |
| 5,026,016 | 6/1991 | Lisowski | 248/225.1 X |
| 5,103,997 | 4/1992 | Shillington et al. | 248/225.1 X |

Primary Examiner—Jacob K. Ackun, Jr.
Attorney, Agent, or Firm—Richard W. Lavin

[57] ABSTRACT

An apparatus for storing used medical needles includes a storage housing member for storing the used medical needles, the housing member including a flange portion for supporting the housing member on a supporting surface enabling an attendant to insert used needles into the housing member with one hand. There is also disclosed a portable support member for capturing the flange portion to rigidly support the housing member enabling one hand operation for inserting used medical needles into the housing member.

11 Claims, 12 Drawing Sheets

APPARATUS FOR STORING USED MEDICAL NEEDLES

BACKGROUND OF THE INVENTION

The present invention is directed to storage receptacles and more particularly to a method and apparatus for storing used medical needles. In the use of medical needles for drawing blood and bodily fluids from patients, it is well recognized that the disposal of such needles is critical in preventing the spread of highly contagious diseases such as AIDS and various forms of hepatitis to the medical technician. One popular type of medical needle in common use today is the butterfly-type rigid needle which includes gripping side strips and an attached tubing for transmitting the fluids to a suitable reciprocal when in use. The attached tubing can serve to provide a whipping action causing the needle to precariously flip around, out of control. In some instances, the needle cannot be immediately disposed of after removal from the patient. This is especially true in the practice of hemodialysis where the immediate concern of the technician is the control of the bleeding from the vacated needle site. More often than not, the used needle is precariously laid either in the patient's lap or on the floor where the needle tip is exposed.

A variety of devices and systems have been propose to prevent possible needle sticks. Examples of such devices can be found in U.S. Pat. Nos. 4,631,058; 4,758,229; 4,917,342; 4,935,012; 4,969,876; 5,017,189; 5,037,400 and 5,046,612. U.S. Pat. Nos. 4,820,282; 4,935,011 and 5,061,250 disclose the use of a sheath to retract the needle, but are subject to the same objection cited above.

It is therefor a principal object of the present invention to provide a method and apparatus for storing used medical needles in which the used needle can be safely inserted into a storage receptacle using only one hand.

It is another object of this invention to provide a support member for a storage member for storing used medical needles which requires only one hand to store the needles in the storage member.

It is a further object of this invention to provide a low cost storage member for storing used medical needles.

SUMMARY OF THE INVENTION

There is provided, in accordance with the present invention, a method and apparatus for storing used medical needles in which the needles include a sharp needle tip portion, a main body portion and a tubing member extending from the body portion for transporting fluids from the needle tip portion. The apparatus includes a box-like storage housing having a main storage area for storing the body portion of the needle, an enclosed forward portion extending outwardly from the main storage area for storing the needle tip portion of the needle and a hinged cover member for covering the main storage area after the used medical needle has been stored in the storage housing. A rear wall portion of the storage housing includes a slot into which the tubing member of the used needle is inserted and which is restrained by the slot. The storage housing includes a flange portion extending horizontally outwardly from the front edge of the storage housing for balancing the storage unit on a supporting surface enabling the used needle to be inserted into the storage housing using only one hand. A tray member associated with the storage housing includes an elongated shaped reduced portion including a cavity portion for capturing the flanged portion of the storage housing for rigidly supporting the storage housing while a used medical needle is being inserted into the storage housing with only one hand. A second embodiment of the apparatus includes the flange portion having a pair of cutout edge portions which engage and capture a pair of pin members extending outwardly from the tray member for rigidly securing the storage housing to the tray member.

BRIEF DESCRIPTION OF THE DRAWINGS

Additional advantages and meritorious features of the present invention will become more apparent and fully understood from a reading of the following detailed description and appended claims when read in conjunction with the drawings wherein like reference numerals indicate like or corresponding elements throughout the several views and wherein:

DETAILED DESCRIPTION OF THE PREFERRED EMBODIMENT

Figure 1:
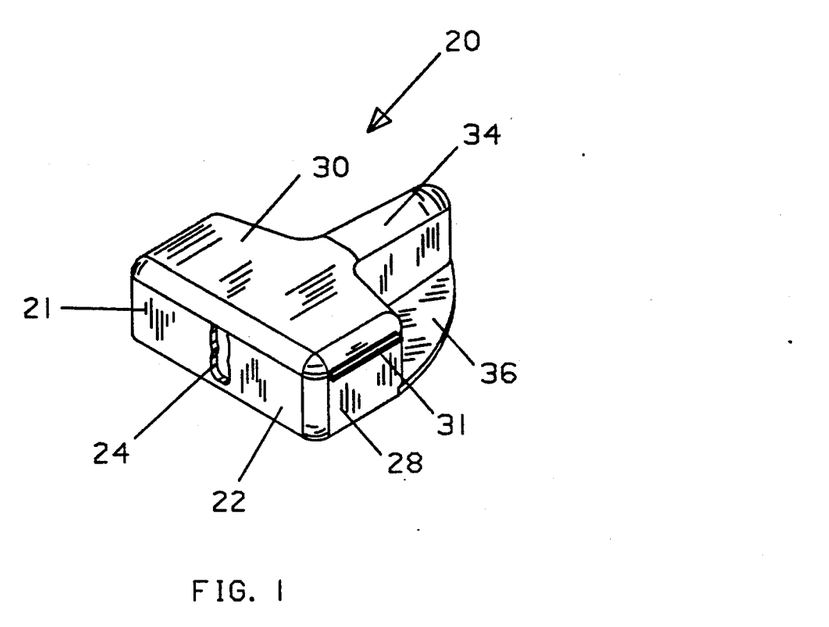
FIG. 1 is a top rear perspective view of the storage apparatus of the present invention shown with the cover in the closed position.
Figure 2:
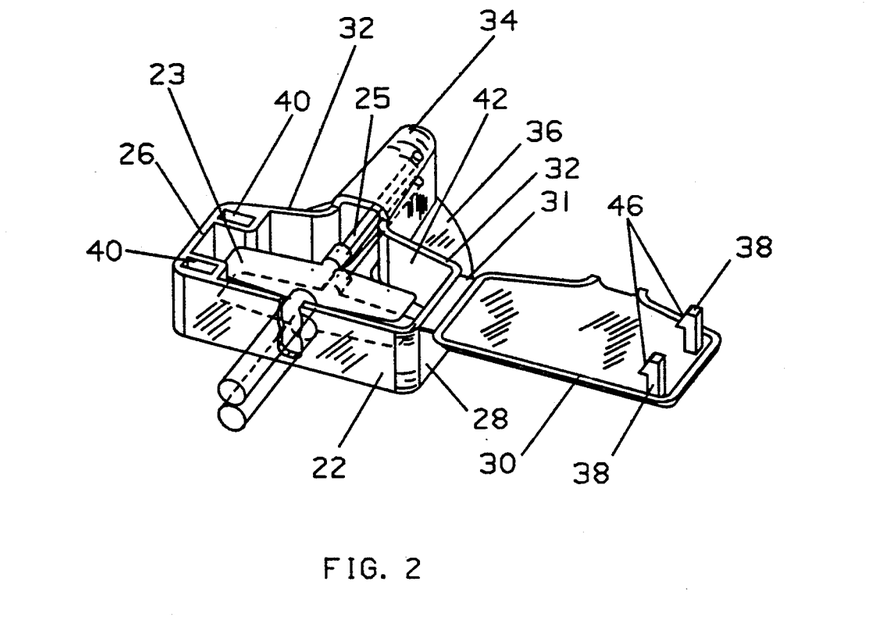
FIG. 2 is a top rear perspective view of the storage apparatus of the present invention shown with the cover in the open position with a pair of butterfly-type needles mounted in a stored position within the storage apparatus.
Figure 4:
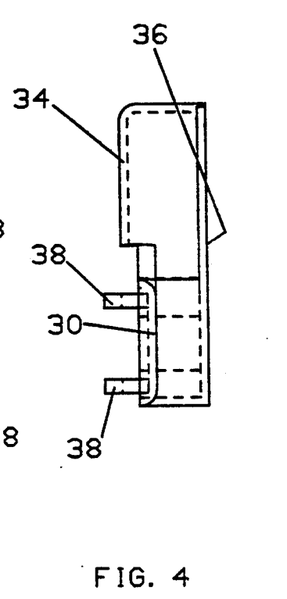
FIG. 4 is right side view of the storage apparatus shown in FIG. 3.

Referring now to FIGS. 1 and 2 of the drawings, there is shown a rear perspective view of the storage apparatus of the present invention which is generally indicated by the numeral 20 and which includes a box-like storage housing member 21 having a rear wall portion 22 including a vertically oriented slot 24, a pair of side wall portions 26, 28 and a slightly curved front wall portion 32 forming a main storage area 42 (FIGS. 2 and 4). The box-like storage housing member has a bottom wall portion and a top wall portion extending part way along the top of the box-like storage member as most clearly seen in FIG. 2. As shown in FIG. 2, one type of medical needle that may be stored in the present invention is the well known butterfly-type needle comprising of a needle tip portion 25, flexible gripping side strips 23 and a tube member 27 secured to the rear of the flexible portion 23. When the needle is inserted into the housing member 21, the tube member 27 will be inserted into the slot 24 in the rear wall portion 22. The slot 24 has a width which is narrower than the width of the tube member 27 allowing the slot to restrain the tube member in a locked position.

Figure 3:
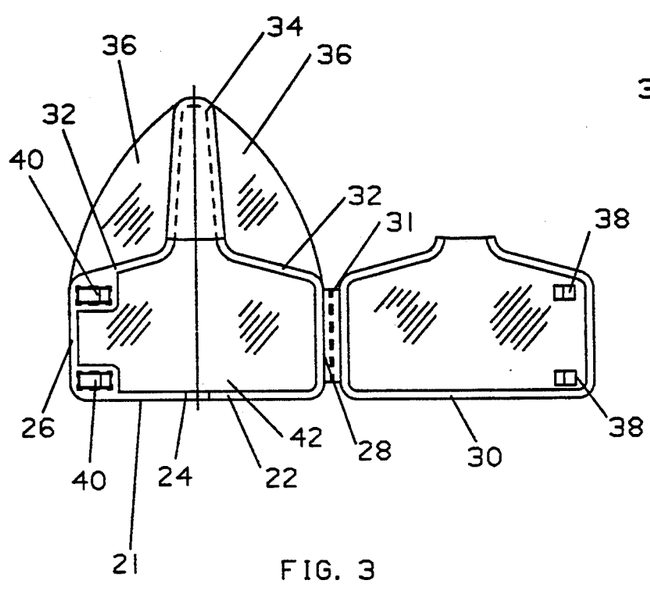
FIG. 3 is a top view of the storage apparatus with the cover member in an open position.
Figure 5:
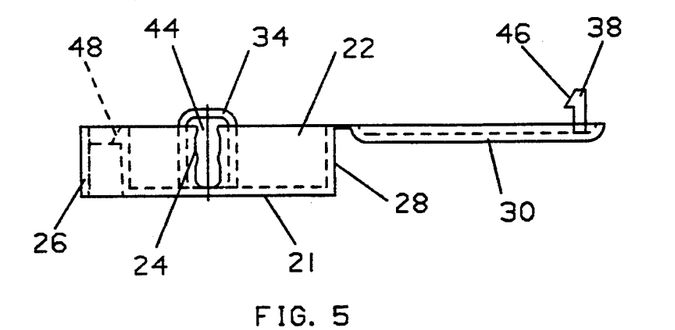
FIG. 5 is a rear end view of the storage apparatus shown in FIG. 3.
Figure 6:
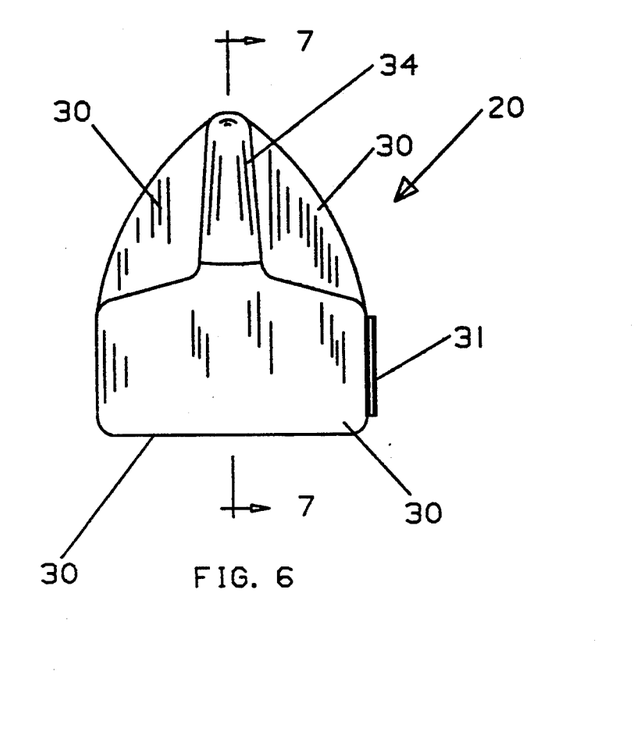
FIG. 6 is a top view of the storage apparatus shown with the cover in a closed position.
Figure 7:
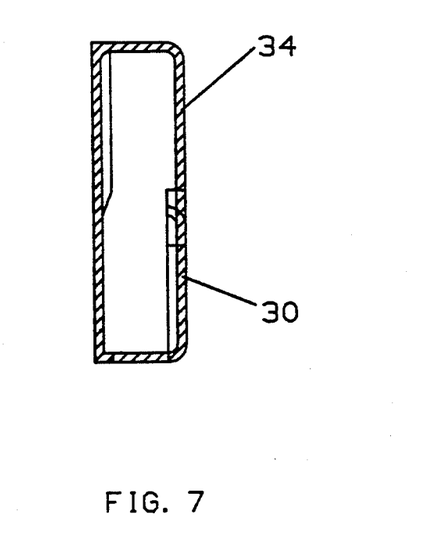
FIG. 7 is a side sectional view of the storage apparatus taken on lines 7—7 of FIG. 6.
Figure 8:
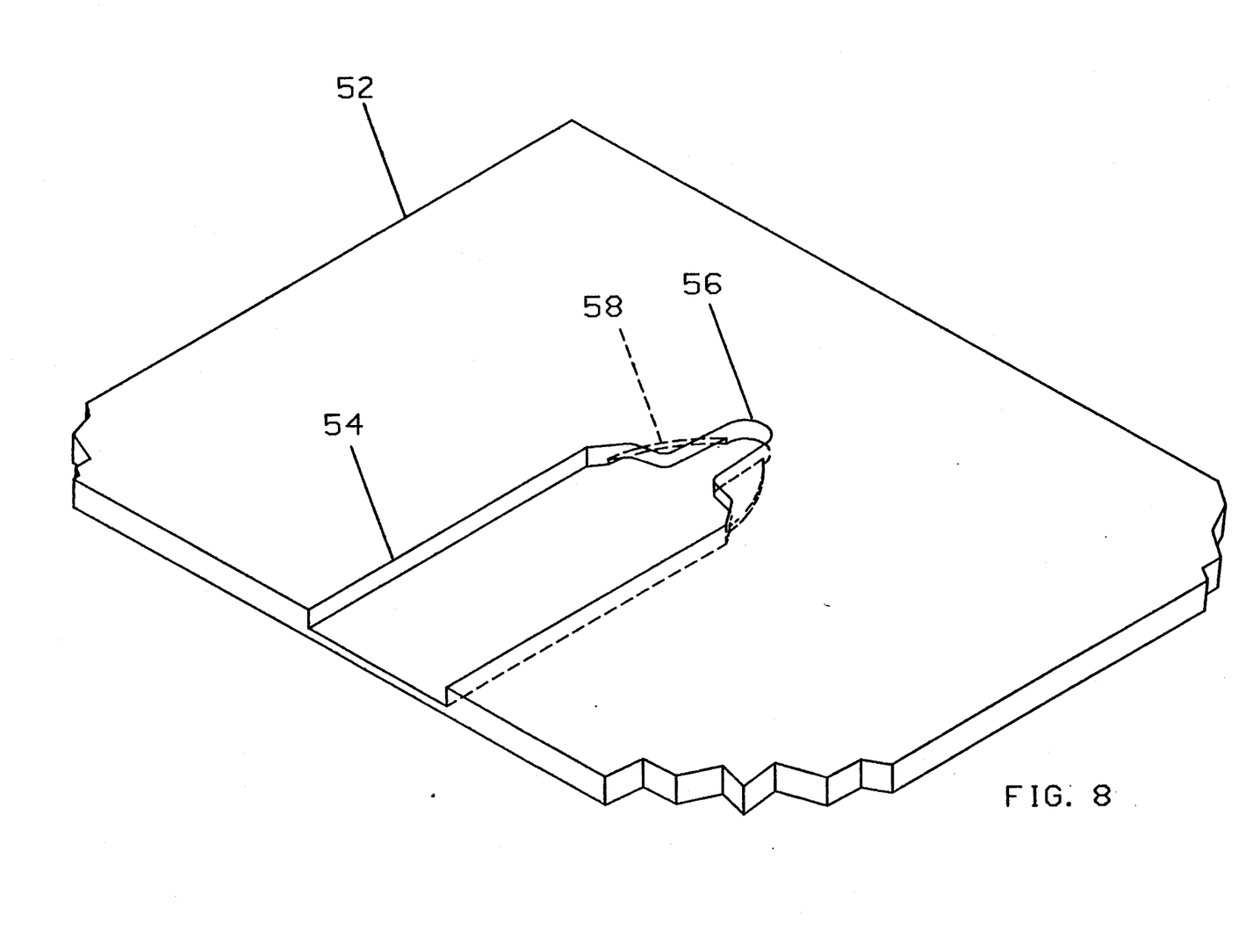
FIG. 8 is a top rear perspective view of the support tray showing the recessed portion of the tray.
Figure 9:
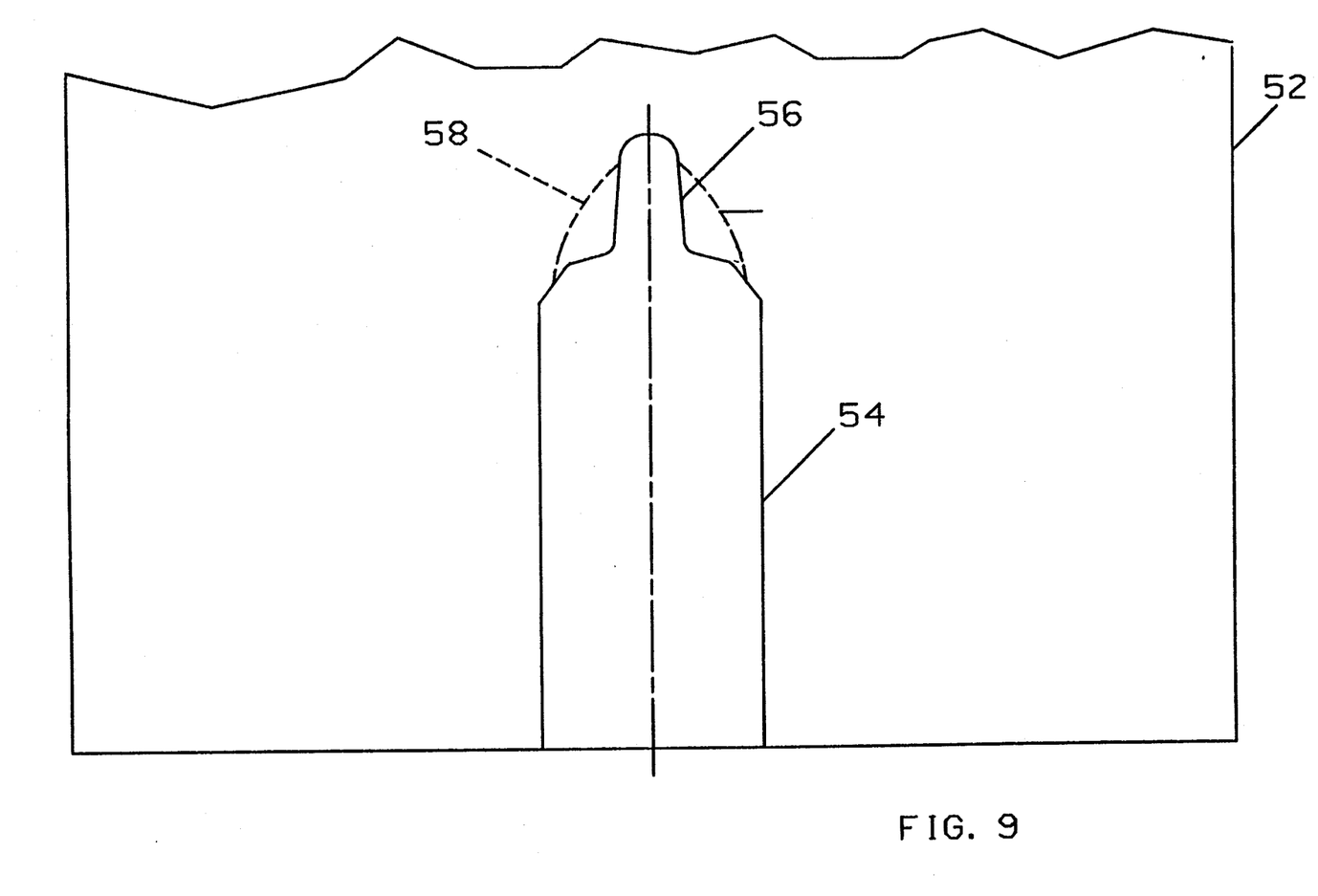
FIG. 9 is a top view of the support tray.
Figure 10:
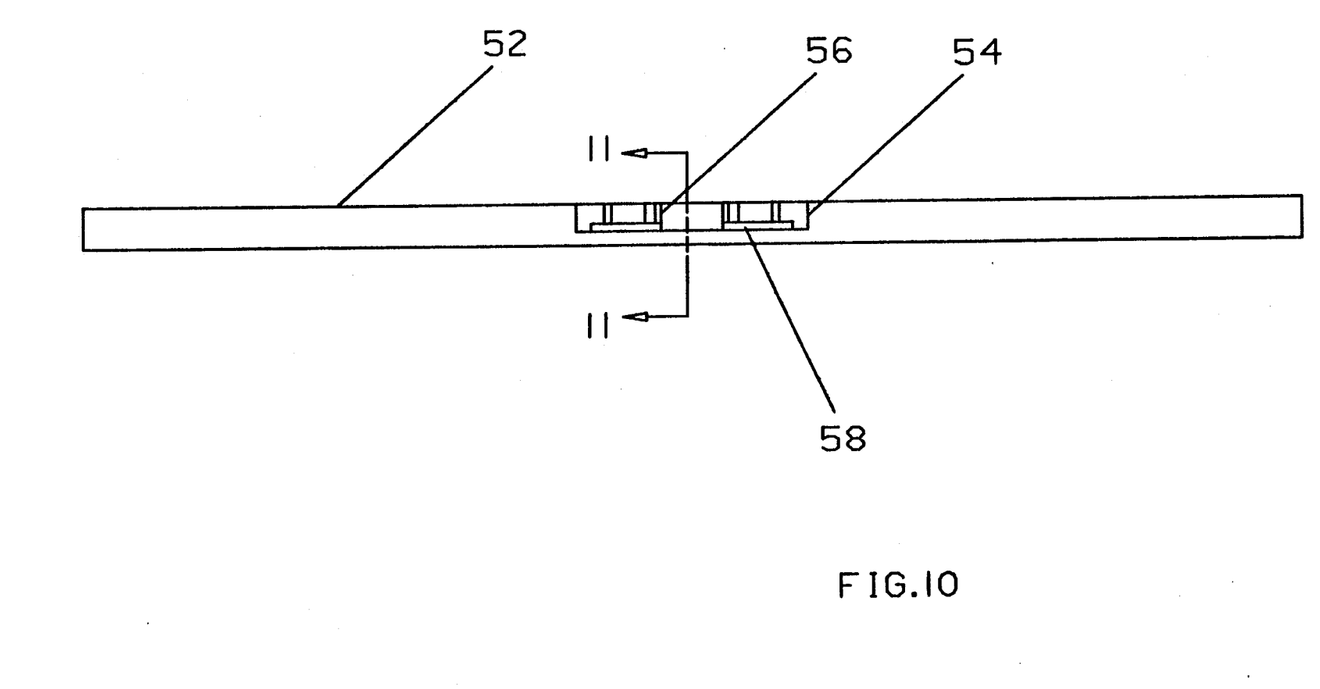
FIG. 10 is a rear end view of the support tray.
Figure 11:
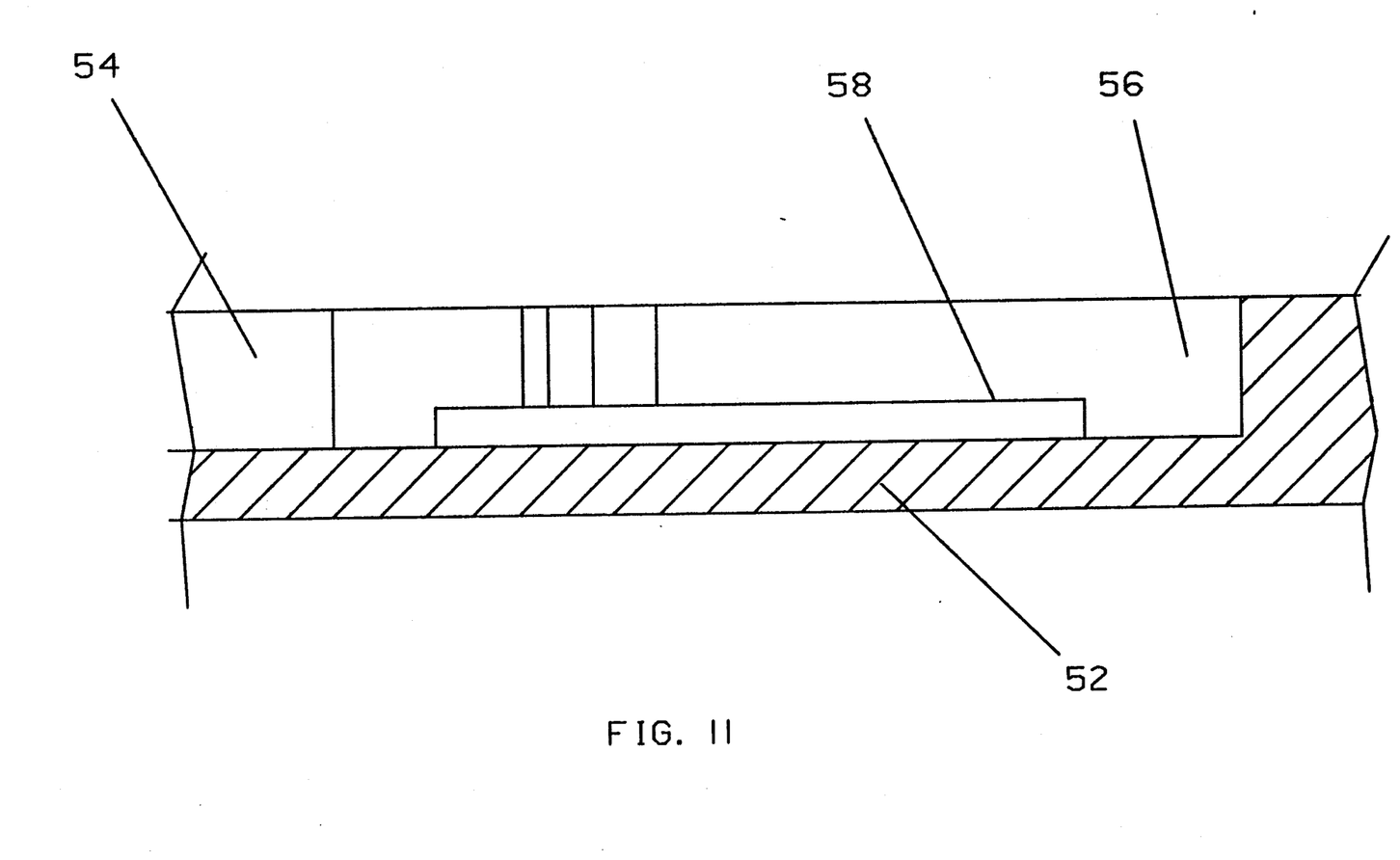
FIG. 11 is an enlarged partial side sectional view of the recessed portion of the support tray taken on lines 11—11 of FIG. 10.

The storage apparatus 20 further includes a cover member 30 hinged to the side wall portion 28 of the housing member by a hinge member 31 (FIG. 3). In the present embodiment, the housing member 21 and the cover member 30 are molded of polyethylene plastic material. The cover member 30 includes a pair of clip members 38 (FIGS. 2, 3 and 4) having a hook portion 46 which is positioned within cavities 40 located in the housing member 21 adjacent the side wall portion 26 and which resiliently engage detent portions 48 (FIG. 5) extending outwardly from the walls of the cavities 40 to secure the cover member 30 to the housing member 21. This construction locks the cover member in a closed position after the used needles have been inserted into the housing member and allows the cover member to be moved to a closed position using only one hand.

Extending outwardly from the front wall portion 32 of the housing member 21 is a hollow needle capture nose portion 34 (FIGS. 1-7 inclusive) which, as shown in FIG. 3, terminates in a pointed end for capturing the tip of the used medical needle portion 25 {FIG. 2} eliminating any possibility of the attending technician being stuck by the tip. Extending outwardly from the lower end of both sides of the nose portion 34 is an elliptical shaped flange portion 36. As will be described more fully hereinafter, the flange portion 36 is utilized to support the housing member on a supporting surface and to rigidly secure the housing member 21 to a support member allowing used medical needles to be inserted into the housing member 21 with one hand.

Referring now to FIGS. 8-11 inclusive, there are shown various views of a support tray member 52 used to rigidly support the housing member 21. The tray member 52 comprises a plano member having a longitudinally extending recessed portion 54. In the present example, the tray member 52 may be composed of a plastic material such as Plexiglas, a trademark of the Du Pont Corp. of Wilmington, Del. or any other type of rigid plastic material. The recessed portion 54 has a nose portion 56 (FIGS. 9 and 11) which is shaped similar to the configuration of the nose portion 34 of the housing member 21 (FIG. 3). The recessed portion 54 includes an undercut portion 58 (FIGS. 9-11 inclusive) having a configuration similar to the configuration of the flange portion 36 of the housing member. In the present embodiment, the tray member 52 is 0.375 inches thick which allows the recessed portion 54 to have a depth of 0.250 inches and the undercut portion 58 to have a thickness of 0.075 inches. The recessed portion 54 has a width of 2.097 inches while the housing member has a width of 1.85 inches.

Figure 12:
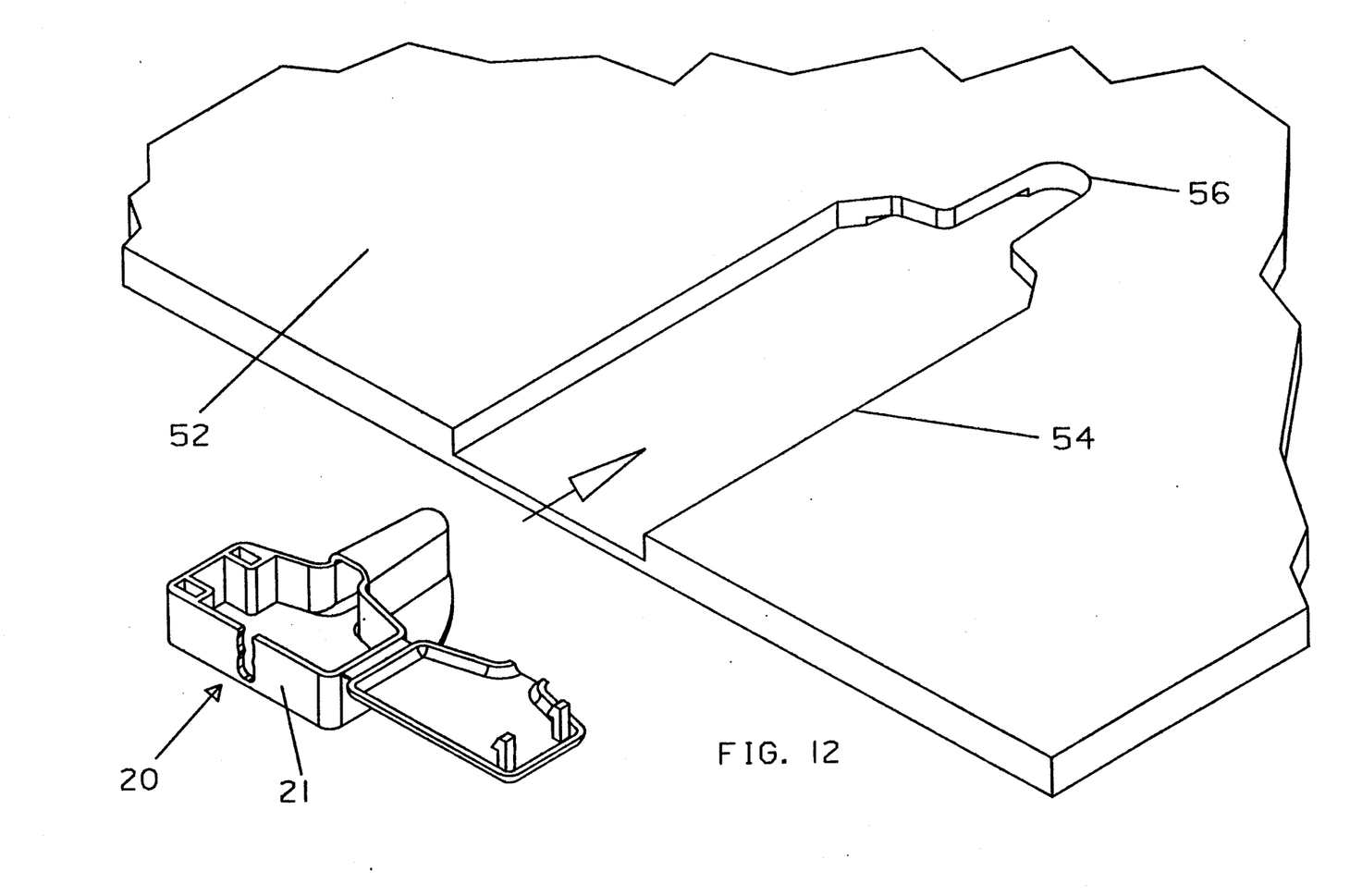
FIG. 12 is a top rear perspective view of the support tray showing the position of the storage apparatus prior to insertion within the recessed portion of the tray.
Figure 13:
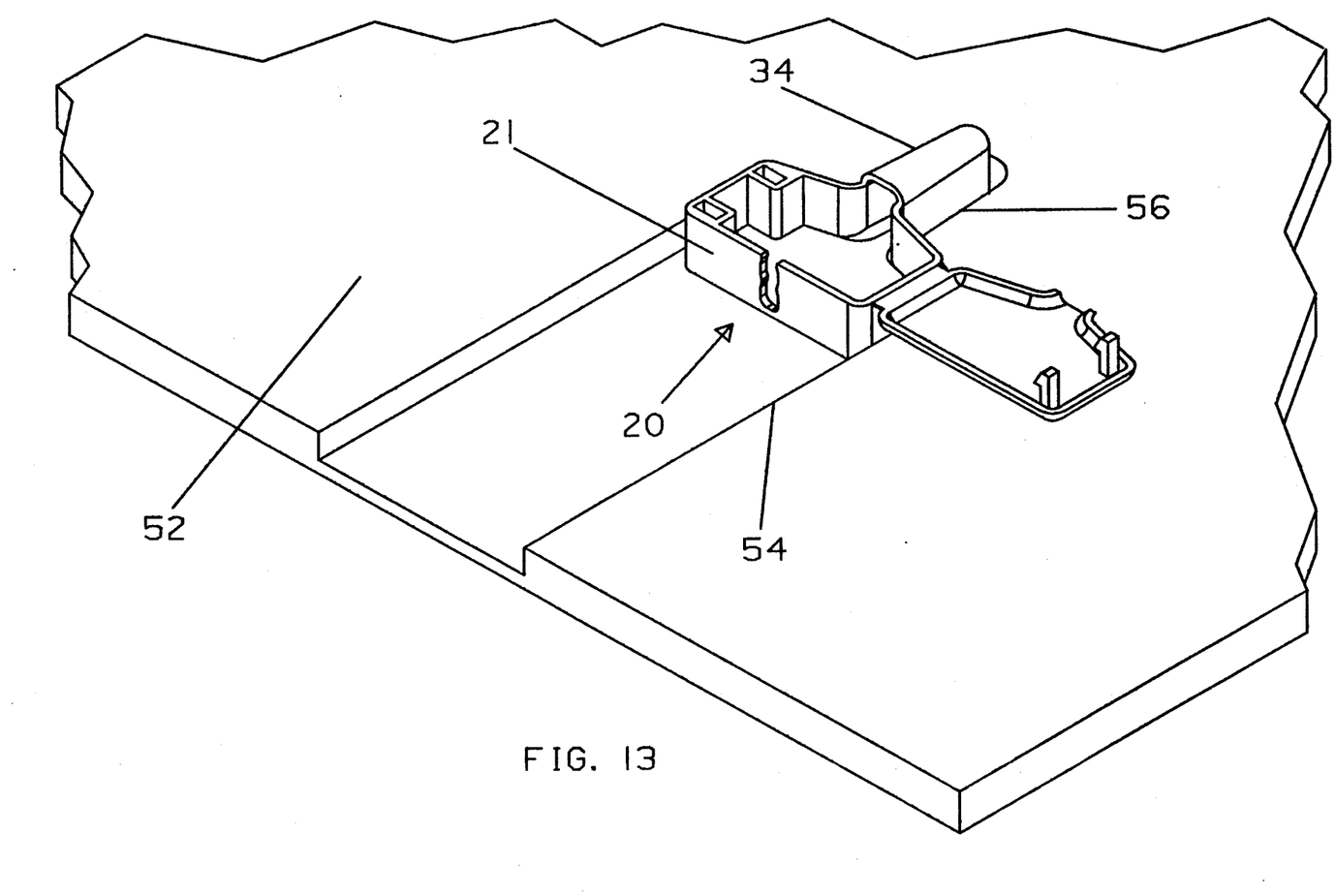
FIG. 13 is a top rear perspective view of the support tray showing the storage apparatus inserted into the recessed portion of the tray.

In the operation of the present invention, the technician may position the housing member 21 on a supporting surface enabling the flange portion 36 to support the housing member while storing the used medical needles in the housing member. Where the tray member 52 is to be used, the housing member is positioned adjacent the entrance to the recessed portion 54 of the tray member 52 {FIG. 12} after which the nose portion 34 of the housing member 21 is moved through the recessed portion 54 and into the nose portion 56 with the flange portion 36 of the housing member positioned within the undercut portion 58 thereby rigidly mounting the housing member in the tray member 52. In disposing of the used medical needles in both instances, the technician will position the needle tip portion 25 {FIG. 2} within the nose portion 34 of the housing member 21 engaging the nose portion and using such engagement as a support, will rotate the needle to position the flexible strips portion 23 of the needle within the storage area 42 of the housing member allowing the tube member to be snapped into place in the slot 24 (FIG. 2) in the rear wall portion 22 of the housing member using only one hand. It will be seen that this construction allows the technician to insert the used medical needle into the housing member using only one hand while allowing the other hand to be used to stop the bleeding from the vacated needle site. After the used needles have been inserted into the housing member, the technician, while still using only one hand, will rotate the cover member 30 into engagement with the top edge of the housing member allowing the clip members 38 to lock the cover member in a closed position. While the present embodiment shows the housing member storing a maximum of two medical needles, it is obvious that the housing member can be constructed to accommodate one or more than two needles.

Figure 14:
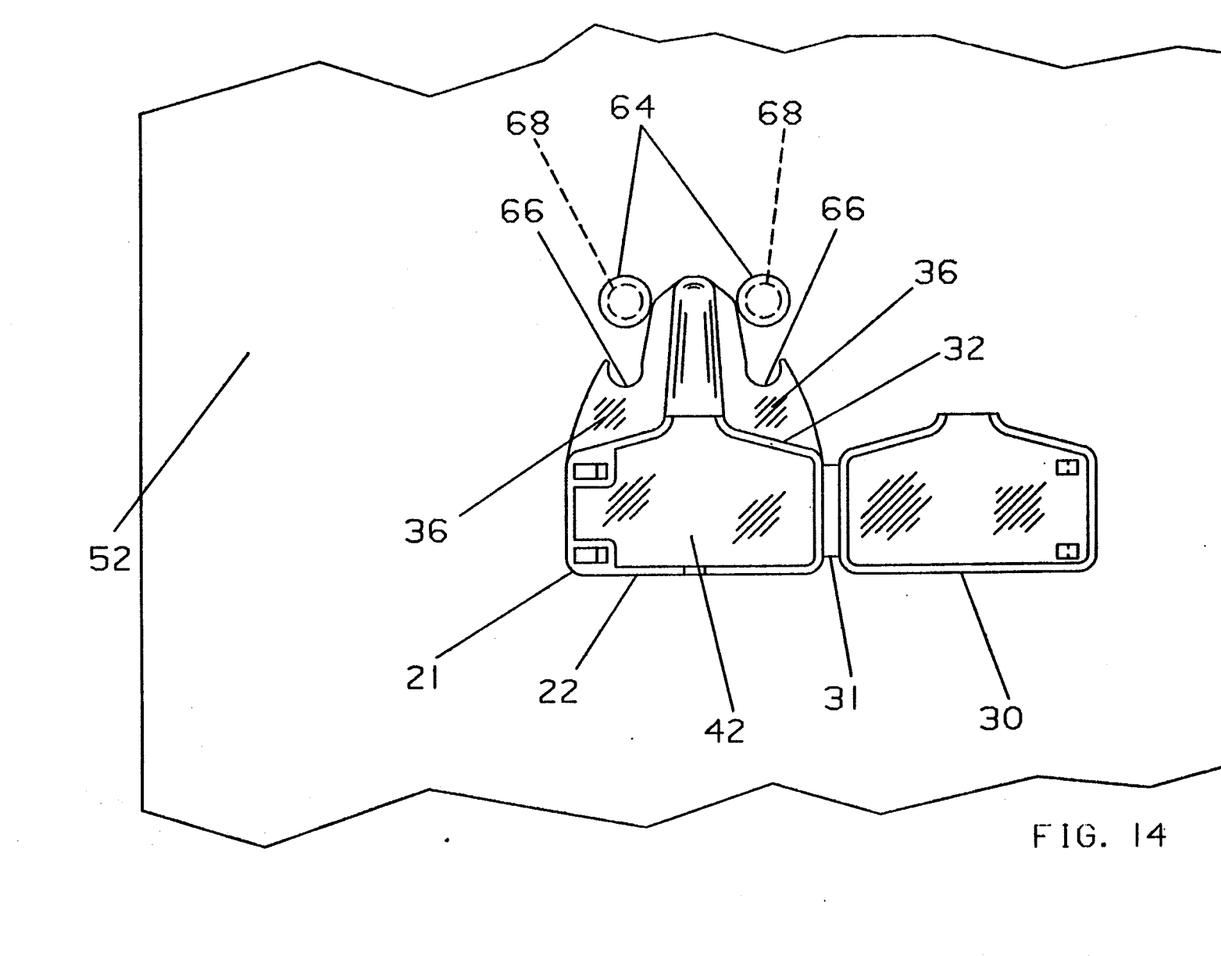
FIG. 14 is a top view of a second embodiment of the support tray showing the storage apparatus prior to engagement with a pair of pin members mounted on the support tray.
Figure 15:
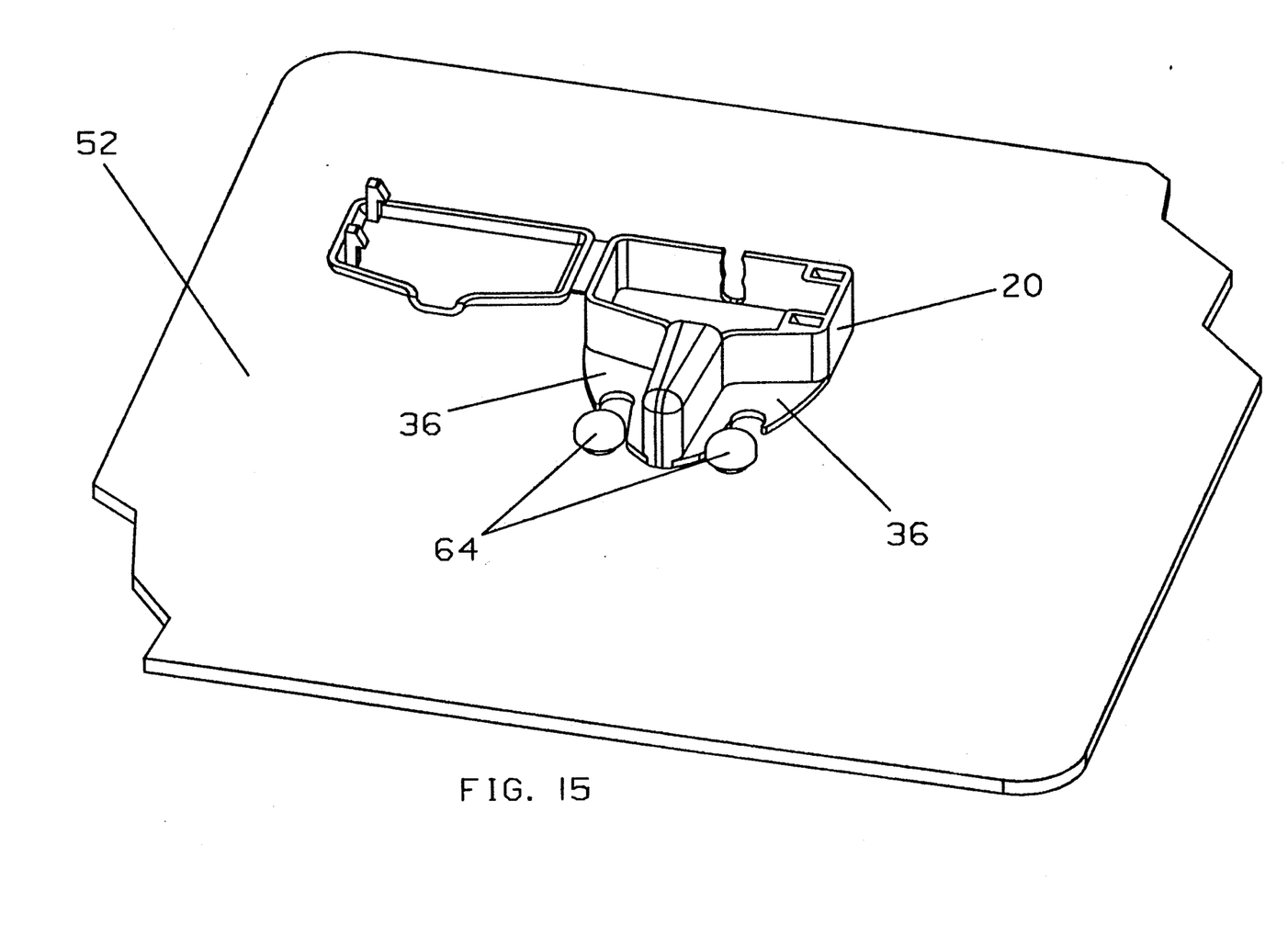
FIG. 15 is a top front perspective view of the storage apparatus and the support tray of FIG. 14.
Figures 16, 17:
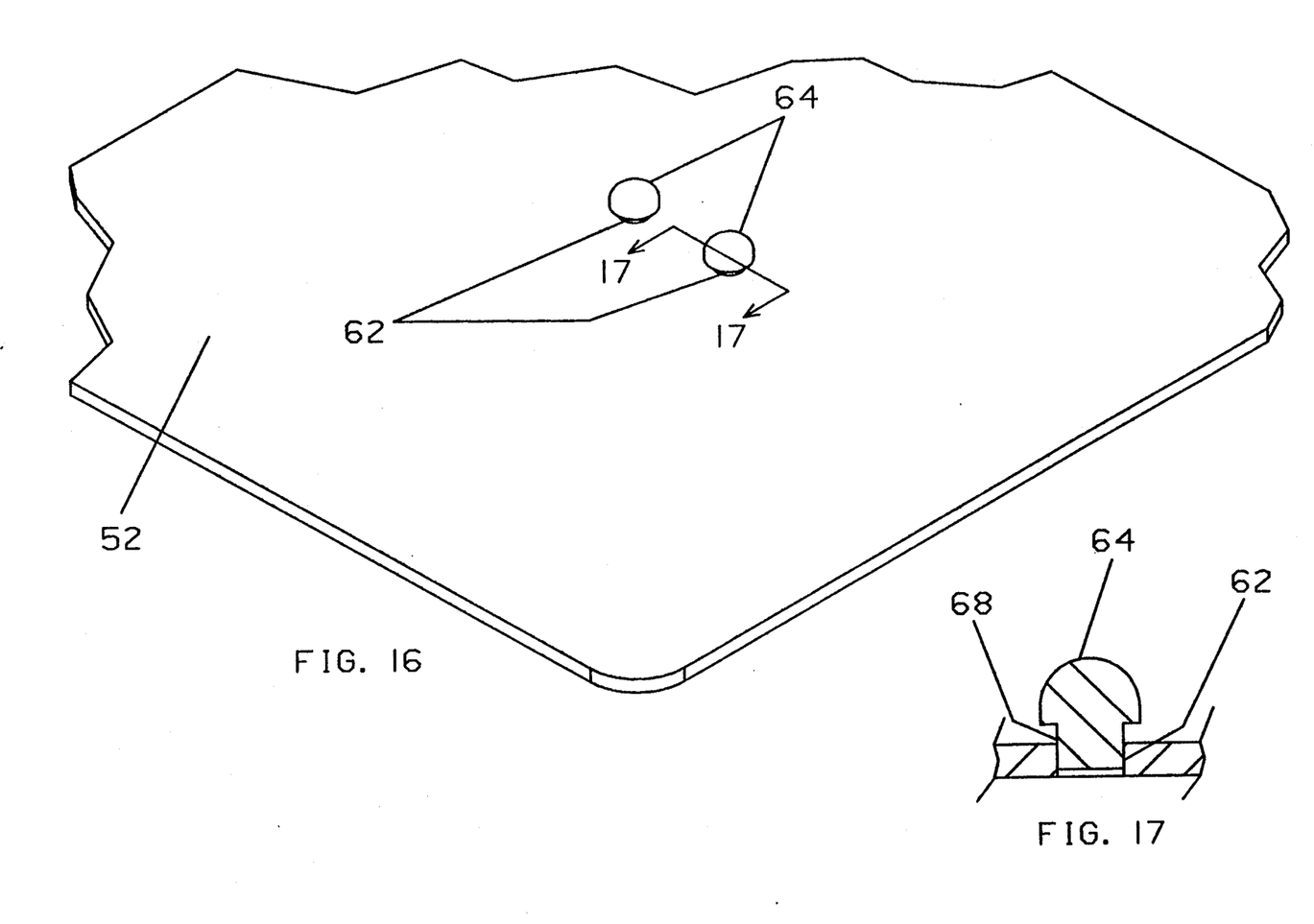
FIG. 16 is a top rear perspective view of support tray of FIG. 14 showing the location of the pin members mounted on the tray.
FIG. 17 is a side sectional view of the pin members mounted on the support tray taken on lines 17—17 of FIG. 16.

Referring now to FIGS. 14-16 inclusive, there is shown a second embodiment of the present invention for storing used medical needles. Mounted within a pair of apertures 62 (FIG. 16) in the tray member 52 are a pair of pin members 64 spaced apart to engage correspondingly positioned cut-out portions 66 (FIG. 14) located in the leading edge of the flange portion 36 for securely mounting the housing member 21 on the tray member 52. As best seen from FIG. 17, the pin members 64 include an undercut portion 68 which engages the flange portion 36. The undercut portions 68 of the pin members 64, which may be constructed of steel, are positioned on the tray member 52 to provide a slight interference fit with the cutout portions 66 of the flange portion 36 allowing the flange portion 36 to snap into engagement with the pin members 64 thereby rigidly mounting the housing member on the tray. After the used needles have been inserted into the storage apparatus 20 and the cover member 30 had been moved to a closed position, the storage apparatus can be disposed of in an appropriate container.

While the salient features of the invention have been illustrated and described, it should be readily apparent to those skilled in the art that many changes and modifications can be made in the invention presented without departing from the spirit and true scope of the invention. Accordingly, the present invention should be considered as encompassing all such changes and modifications of the invention that fall within the broad scope of the invention as defined by the claims.

What is claimed is:

1. An assembly for storing used medical needles comprising in combination:

a plane support member extending in a generally horizontal direction having an elongated slotted portion in a top surface of the support member;

an elongated housing member for receiving and storing used medical needles, said housing member having opposed side wall portions a rear wall portion, a front wall portion, and a bottom wall portion, a top wall portion attached to said front wall portion and to said side wall portions to form an enclosed front portion of said elongated housing member for storing the tips of used medical needles said top wall portion extending only partially along the length of said elongated housing member to form a rear open portion of said elongated housing member, said rear open portion defined by said bottom wall portion, said side wall portions, and said rear wall portion, a flange portion extending outwardly in a direction generally parallel to said bottom wall portion form the side wall portions adjacent the front portion for engaging the slotted portion of the support member upon insertion of the flange portion of the housing member within the slotted portion of the support member for rigidly supporting the housing member in a generally horizontal position on the support member for allowing a used medical needle to be inserted within the housing member using only one hand; and a cover member hinged to a top edge of one of the side wall portions wherein said cover member is rotatable to a closed position in which said cover member covers said rear open portion of the housing member for storing any used medical needles positioned within the housing member.

2. The assembly of claim 18 in which the rear wall portion of the housing member has a vertically oriented slot for insertion of one end of a used medical needle, said slot for engaging and holding the used medical needle inserted within the housing member 3. The assembly of claim 1 in which said housing member includes a recessed portion and said cover member includes a depending clip member which is inserted into said recessed portion for locking the cover member in said closed position on said rear open portion when rotated toward the closed position.

4. The assembly of claim 1 in which said slotted portion of the support member further includes an undercut portion for receiving the flange portion for rigidly securing the storage member to the support member.

5. The assembly of claim 1 in which the flange portion and the slotted portion have mutually contiguous curved edges for accommodating the flange portion within the slotted portion of the support ember.

6. The assembly of claim 4 in which the flange portion and the undercut portion have mutually contiguous curved edges for accommodating the flange portion within the undercut portion of the support member.

7. In combination, a medical needle having a needle tip portion, a main body portion and a tube portion extending form the rear of the body portion;

a plano support member mounted in a generally horizontal direction having a pair of abutment members extending upwardly form an upper surface of said plan support member;

an elongated T-shaped box-like storage member having front and rear portions for storing used medical needles, said front portion having a forwardly extending nose portion a part of which is enclosed by a front wall portion, opposed side wall portions, a bottom wall portion and a top wall portion of said storage member for receiving the needle tip portion of the used medical needles, said nose portion having a flange portion extending outwardly from the lower edge of the opposed side wall portions and the front wall portion and generally parallel to said bottom wall portion for engaging the abutment members of the support member for rigidly supporting the storage member in a generally horizontal position allowing a used medical needle to be inserted within the storage member using only one hand; and said rear portion defined by a rear wall portion and said opposed side wall portions and bottom wall portion of sad storage member, said rear portion and another part of said nose portion adjacent thereto not having a top wall portion at a top thereof wherein an opening for storage member is formed, and a cover member hingedly secured to a top edge of one side wall member at said rear portion, said cover member being rotatable to a closed portion wherein said cover member covers said opening.

8. The combination of claim 7 in which said rear wall portion includes a vertically extending slot for engaging and securing the tube portion of a used medical needle when inserted in said storage member, said slot for storing a plurality of used medical needles.

9. The combination of claim 7 in which said storage member includes a cavity portion positioned adjacent the side wall portion opposite to the side wall portion which rotatably supports the cover member, said cover ember includes a depending engaging portion for engaging the cavity portion for securing the cover member to a top edge of the storage member in an enclosed position.

10. The combination of claim 7 in which said flange portion includes a pair of cutout portions for engaging and capturing the abutment members for rigidly securing the storage member to the support member.

11. The combination of claim 10 in which said abutment members include a recessed portion for engaging the cutout portions of said flange portion enabling the flange portion to be held by said recessed portion for rigidly securing the storage member to the support member.

* * * * *